United States Patent [19]

Said

[11] 4,144,238
[45] Mar. 13, 1979

[54] PROCESS FOR THE PRODUCTION OF PURE WHITE 2-CHLORONICOTINIC ACID

[75] Inventor: Adel Said, Brig, Switzerland

[73] Assignee: Lonza, Ltd., Gampel, Switzerland

[21] Appl. No.: 784,323

[22] Filed: Apr. 4, 1977

[30] Foreign Application Priority Data

Apr. 2, 1976 [CH] Switzerland .......................... 4124/76

[51] Int. Cl.² ........................................... C07D 213/55
[52] U.S. Cl. ................................................... 546/318
[58] Field of Search ................................. 260/295.5 R

[56] References Cited

FOREIGN PATENT DOCUMENTS 80209 10/1971 German Democratic Rep. ... 260/295.5 R

Primary Examiner—Alan L. Rotman
Attorney, Agent, or Firm—Fisher, Christen & Sabol

[57] ABSTRACT

The process for the production of 2-chloronicotinic acid from nicotinic acid-N-oxide, characterized in that the 2-chloronicotinic acid chloride is distilled off from the reaction mixture and the distillate is allowed to flow into water at a temperature of 40° to 100° C. The 2-chloronicotinic acid chloride is hydrolized to the 2-chloronicotinic acid, which precipitates in a pure white crystalline form.

5 Claims, No Drawings

4,144,238

PROCESS FOR THE PRODUCTION OF PURE WHITE 2-CHLORONICOTINIC ACID

BACKGROUND OF THIS INVENTION

1. Field of This Invention

This invention relates to a process for the production of 2-chloronicotinic acid from nicotinic acid-N-oxide.

2. Prior Art 2-chloronicotinic acid has been produced from nicotinic acid-N-oxide with $PCl_5$ in the presence of $POCl_3$. It is also known to react (convert) nicotinic acid-N-oxide with phosphorous oxychloride in the presence of a tertiary organic amine or of a carboxylic acid amide (East German Pat. No. 80,209). However, in the case of such known process, colored end products result which cannot be decolored, even with repeated recrystallization. Purifying processes using activated charcoal, despite the use of high portions of activated charcoal related to the product to be purified, do not achieve the desired goal. According to East German Pat. No. 80,209, additions of alkalines (1yes) is necessary, but, which with regard to purity of the product, has no advantageous effect and leads to increased loading of the effluent.

BROAD DESCRIPTION OF THIS INVENTION

An object of this invention is to achieve a process for the production of a pure white 2-chloronicotinic acid in a good yield and at a relatively small cost. Other objects and advantages of this process are set out herein or are obvious herefrom to one ordinarily skilled in the art.

The objects and advantages of this invention are achieved by the process of this invention.

This invention involves the process of distilling 2-chloronicotinic acid chloride out of the reaction mixture. The reaction mixture normally results from the conversion of nicotinic acid-N-oxide into 2-chloronicotinic acid chloride. The distillate is permitted or caused to flow into water at a temperature of 40° to 100° C., preferably at a temperature of 90° to 100° C., whereby the 2-chloronicotinic acid chloride is hydrolyzed to the 2-chloronicotinic acid, which is in pure white crystalline form.

The process of this invention permits the conversion of 2-chloronicotinic acid chloride, which has been produced by a known process, in a simple and easy manner into pure white 2-chloronicotinic acid.

Whenever 2-chloronicotinic acid chloride has been made using phosphorus oxychloride, for example, according to the process of East German Pat. No. 80,209, where the main quantity of excess phosphorus oxychloride is distilled off under vacuum, and then the residue is allowed to flow into water below 40° C., this invention distills off the excess phosphorus oxychloride followed by distillation off of the 2-chloronicotinic acid chloride, and then the 2-chloronicotinic acid chloride is permitted to flow into water at a temperature of 40° to 100° C., preferably at 90° to 100° C. At the same time the 2-chloronicotinic acid chloride is hydrolyzed. After cooling, the acid chloride precipitates out as a pure white crystalline material. In order to remove any 6-chloronicotinic acid, developed possibly as a by-product, the 2-chloronicotinic acid is recrystallized from a methyl alcohol-water mixture.

The quality of the pure product is very good and its content is more than 99 percent.

As used herein, all parts, ratios, percentages and proportions are on a weight basis unless otherwise stated or otherwise obvious to one ordinarily skilled in the art.

EXAMPLE 1

Comparison Example 70 gm. of nicotinic acid-N-oxide was suspended in 300 ml of $POCl_3$. Then 50 gm. of triethyl amine was added drop by drop at room temperature, whereby the nicotinic acid-N-oxide dissolved at about 50° C. (the temperature rise occured due to an exothermic reaction). Then the solution was heated in a water bath at 100° C. for another 4 hours. The main quantity of excess phosphorus oxychloride was distilled off under vacuum. The residue was allowed to flow into water at a temperature below 40° C. After addition of diluted caustic soda solution, the 2-chloronicotnic acid precipitated at a pH value of 2.0 to 2.5. The product had a melting point of 173° to 175° C. (Kofler). The product (2-chloronicotinic acid) yield amounted to 65 to 70 percent of theory.

The product was processed as follows: the raw product was recrystallized from $MeOH/H_2O$ by the addition of activiated charcoal (20 percent). It was then dissolved in MeOH (only a part of the contaminates remained undissolved), mixed with activated charcoal (20 percent) and filtered off. The filtrate was evaporated to dryness. The dried filtrate was suspended in a little water, filtered and dried. A yellowish article in a 44 percent yield was obtained. The goods have a content of 99 percent. Whenever one wishes to obtain a still only slightly yellowish article, one must recrystallize the product after the methanol treatment from $MeOH/H_2O$. The yield was 39 to 42 percent.

In spite of the expensive process used, which had extensive product losses, only a light yellow to grayish yellow product was obtained. The process of this example had the following disadvantages:

(a) the product was colored;
(b) the raw product had to be recrystallized three times; and
(c) the consumption of activated charcoal was high.

EXAMPLE 2

70 gm. of nicotinic acid-N-oxide was suspended in 300 ml of $POCl_3$. 51.5 gm of triethylamine was added drop by drop at ambient temperature in such a way, that the reaction temperature did not exceed 60° C. The solution was heated to 110° C. for 3 hours. Subsequently, phosphorus oxychloride was distilled off at 50 torr and the 2-chloronicotinic acid chloride was distilled off at 10 to 12 torr. The distilled acid chloride was permitted to flow into the water at 90° to 100° C., whereby it was hydrolized. After cooling, the acid precipitated out. The precipitated acid was obtained in a yield of 57 percent and was crystalline and pure white. The crude acid was recrystallized to remove removal the 6-chloronicotinic acid from $MeOH/H_2O$ (1:1). The total product yield was 45 to 50 percent. The product had a melting point of 181° to 182° C. (decomposition).

As 2-chloronicotinic acid is used in the production of pharmaceuticals, it is very important to have very pure 2-chloronicotinic acid. The process of this invention achieves such, whereas the prior art processes do not achieve the high degree of purity.

What is claimed is:

1. The process for the production of 2-chloronicotinic acid from nicotinic acid-N-oxide, characterized in that the 2-chloronicotinic acid chloride is distilled off from the nicotinic acid-N-oxide reaction mixture and the distillate is allowed to flow into water at a temperature of 40° to 100° C., whereby the 2-chloronicotinic acid chloride is hydrolyzed to the 2-chloronicotinic acid, which precipitates in a pure white crystalline form.

2. The process as claimed in claim 1 wherein the water is at a temperature between 90° and 100° C.

3. The process as claimed in claim 1 wherein the 2-chloronicotinic acid is recrystallized from a methanol-water mixture.

4. The process as claimed in claim 1 wherein the distillation is effected at a pressure of 10 to 12 torr.

5. The process as claimed in claim 1 wherein phosphorus oxychloride is used in the production and any excess phosphorus oxychloride is distilled off before the 2-chloronicotinic acid chloride is distilled off.

* * * * *